(12) United States Patent  
Meenken

(10) Patent No.: US 11,129,932 B2  
(45) Date of Patent: Sep. 28, 2021

(54) FLUID DRUG CARTRIDGE TYPE IDENTIFICATION

(71) Applicant: Roche Diabetes Care, Inc., Indianapolis, IN (US)

(72) Inventor: Thomas Meenken, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 312 days.

(21) Appl. No.: 16/280,808

(22) Filed: Feb. 20, 2019

(65) Prior Publication Data

US 2019/0175818 A1 Jun. 13, 2019

Related U.S. Application Data

(63) Continuation of application No. PCT/EP2017/071310, filed on Aug. 24, 2017.

(30) Foreign Application Priority Data

Sep. 2, 2016 (EP) ..................................... 16186929

(51) Int. Cl.
*A61M 5/14* (2006.01)
*A61M 5/145* (2006.01)
(Continued)

(52) U.S. Cl.
CPC ...... *A61M 5/1413* (2013.01); *A61M 5/14566* (2013.01); *A61M 5/162* (2013.01);
(Continued)

(58) Field of Classification Search
CPC ............ A61M 5/1413; A61M 5/14573; A61M 5/14566; A61M 5/1402; A61M 5/1408;
(Continued)

(56) References Cited

U.S. PATENT DOCUMENTS 6,743,202 B2* 6/2004 Hirschman ....... A61M 5/14546  
                                                                  604/131  
8,939,930 B2 1/2015 Li et al.  
(Continued)

FOREIGN PATENT DOCUMENTS

JP 2002-518108 A 6/2002  
JP 2013-523295 A 6/2013  
(Continued)

OTHER PUBLICATIONS

International Search Report and Written Opinion of the International Searching Authority, PCT/EP2017/071310, dated Oct. 24, 2017, 22 pages.

*Primary Examiner* — Nathan R Price  
*Assistant Examiner* — Justin L Zamory  
(74) *Attorney, Agent, or Firm* — Bose McKinney & Evans LLP

(57) ABSTRACT

This disclosure provides a method of determining a cartridge type of a cartridge used with a fluid drug injection system having a pump that receives a fluid drug cartridge. The fluid drug cartridge has a barrel filled with a fluid drug solution and a plunger within the barrel that forces the fluid drug solution through an outlet. An actuator of the pump is moved to contact or to move the plunger and a force sensor is used to measure force data during the movement. The force data is descriptive of the force applied to the plunger. A feature signal is determined from the force data. The feature signal can be a force modulation amplitude, a force modulation duration or a force modulation number. The cartridge type is assigned using the feature signal. Also disclosed is a fluid drug injection system and a cartridge for use therewith.

27 Claims, 13 Drawing Sheets

(51) Int. Cl.
    *A61M 5/162*    (2006.01)
    *A61M 5/31*     (2006.01)
    *A61M 5/315*    (2006.01)
    *A61M 5/24*     (2006.01)
    *A61M 5/28*     (2006.01)
    *A61M 5/142*    (2006.01)

(52) U.S. Cl.
    CPC ............... *A61M 5/24* (2013.01); *A61M 5/28* (2013.01); *A61M 5/3129* (2013.01); *A61M 5/31515* (2013.01); *A61M 2005/1402* (2013.01); *A61M 2005/14208* (2013.01); *A61M 2205/10* (2013.01); *A61M 2205/332* (2013.01); *A61M 2205/60* (2013.01); *A61M 2205/6018* (2013.01)

(58) Field of Classification Search
    CPC ...... A61M 2205/60; A61M 2205/6036; A61M 2205/6009; A61M 2205/6018; A61M 2205/6027; A61J 2205/40
    See application file for complete search history.

(56) References Cited

U.S. PATENT DOCUMENTS

| | | |
|---|---|---|
| 2009/0112156 A1 | 4/2009 | Zhao et al. |
| 2011/0264033 A1* | 10/2011 | Jensen ............... G16H 20/17 |
| | | 604/65 |
| 2013/0150802 A1 | 6/2013 | Claughton |
| 2013/0178792 A1 | 7/2013 | Li |
| 2015/0273145 A1 | 10/2015 | Nessel et al. |
| 2015/0302778 A1 | 10/2015 | Helmer et al. |
| 2016/0022916 A1 | 1/2016 | Tran et al. |

FOREIGN PATENT DOCUMENTS

| | | |
|---|---|---|
| JP | 2014-505503 A | 3/2014 |
| JP | 2015-532862 A | 11/2015 |
| WO | WO 99/65548 A1 | 12/1999 |
| WO | WO 2004/052429 A1 | 6/2004 |
| WO | WO 2006/116997 A1 | 11/2006 |
| WO | WO 2009/024562 A1 | 2/2009 |
| WO | WO 2009/083600 A1 | 7/2009 |
| WO | WO 2013/004307 A1 | 1/2013 |
| WO | WO 2013/004308 A1 | 1/2013 |
| WO | WO 2014/128156 A1 | 8/2014 |

* cited by examiner

FLUID DRUG CARTRIDGE TYPE IDENTIFICATION

RELATED APPLICATIONS

This application is a continuation of PCT/EP2017/071310, filed Aug. 24, 2017, which claims priority to EP 16 186 929.2, filed Sep. 2, 2016, the entire disclosure of both of which are hereby incorporated herein by reference in their entirety.

BACKGROUND

This disclosure relates to injection devices for injecting fluid drugs, in particular to the identification of cartridges used for such injection devices.

The maintenance of chronic diabetes or other medical conditions may require the regular injection of fluid drugs such as insulin. For example, an insulin pump in conjunction with an infusion set may be used to inject insulin into a subject based on a predetermined schedule, based on food consumption, and/or based on blood sugar measurements. Some insulin pumps are able to be loaded with different types of cartridges. For example, different types of cartridges may be filled with different types of insulin solution. The concentration of insulin in such solutions may for example vary from cartridge type to cartridge type. The correct volume to inject into a subject is therefore dependent upon the type of cartridge used.

International patent publication WO 2013/004308 A1 discloses detecting an occlusion in an injection device for injecting automatically a medicament, an injection force is measured, a force offset value is deducted from measurements of the injection force, and occlusions are detected based on the measurements having the force offset value deducted.

International patent publication WO 2013/004307 A1 discloses an injection device for injecting automatically a medicament that includes an occlusion detection system with a force measurement unit and two separate occlusion detectors. The occlusion detectors are configured to take force measurements at different respective measurement rates, and to generate occlusion indicating signals based on a set of force measurements taken at the respective measurement rates. The injection device further comprises an alarm generator for generating an occlusion alarm signal in cases where either or both of the occlusion detectors generate an occlusion indicating signal. Two occlusion detectors operating at different measurement rates make it possible to detect occlusions more reliably over a broader range of delivery rates.

International patent application WO 2009/024562 (herein referred to as the '562 application) discloses a medical device with a value sensor. This application discloses an RFID comprising a value sensor such as a pressure sensor integrated with a liquid drug container to enable wireless pressure or other drug relevant parameter value monitoring and code-matching of drug container to a medical delivery device. The '562 application shows in FIG. 6 serrated extensions which are explicitly part of the actuator mechanism 70. The '562 application discloses an RFID chip that incorporates a pressure sensor and is powered by the RFID system. The identification of the cartridge is performed using the RFID chip.

SUMMARY

This disclosure provides for a method of determining a cartridge type, a fluid drug injection system, and a fluid drug cartridge.

Embodiments disclosed herein may provide a method of identifying a cartridge type of a fluid drug cartridge by monitoring the force necessary to move a plunger within a barrel of the fluid drug cartridge as a function of time. The barrel contains a fluid drug solution and the plunger is used to force fluid drug from the fluid drug cartridge.

A fluid drug as used herein encompasses a substance that may be injected to induce a physiological change in a subject. The fluid drug may for example be, but is not limited to: insulin, glucagon, a pain killer, an anticancer drug, and an antibiotic.

The physical structure of the barrel and/or the plunger may be modified such that data may be encoded into the force necessary to move a plunger as a function of time. The region of the force vs time data where data is encoded is referred to herein as a feature signal. For example the feature signal may contain modulations where the force rises and falls as a function of time. Data may be encoded in the form of the number of force modulations, the amplitude of the modulations, and/or the length (duration) of the modulations.

A pump may have an actuator, e.g., a piston for moving the plunger. The measured feature signal may be related to the position of the actuator, the velocity at which the actuator moves, or a function of time. For different actuator velocities, actuator positions, or times, the feature signal may have different amplitude modulations or modulation durations.

In one example, a database or lookup table may be used to compare the feature signal to a list of cartridge types to assign a cartridge type to a fluid drug cartridge. In another example, the feature signal is compared with different example features signals stored in a database. If there is a match between the feature signal and one of the example features signals from the database then a description of the matching feature signal is used to assign the cartridge type.

The identification of the fluid drug cartridge can be performed during different phases of using the fluid drug cartridge. A force sensor may be included in the fluid drug injection system to determine when the actuator engages the plunger. This is known as "force sniffing." For example, structures may be added to the fluid drug cartridge which interact with the actuator before it engages the plunger. These structures may modulate the force in a way which, as described above, encodes data as a feature signal.

Alternatively, the identification of the fluid drug cartridge may be performed during a priming operation. During a priming operation, a fluid drug injection system is primed to remove air bubbles from the system. Priming occurs after the actuator has engaged the plunger. The actuator then moves the plunger a short distance and forces some of the fluid drug system to displace air bubbles. The structure of the fluid drug cartridge can be modified such that as the actuator moves the plunger this short distance the force necessary to move the plunger is modulated. This can be used to encode a feature signal also.

In one aspect, this disclosure provides for a method of determining a cartridge type with a fluid drug injection system. The fluid drug injection system comprises a pump configured for receiving a fluid drug cartridge. The fluid drug cartridge comprises a barrel filled with a fluid drug solution. The fluid drug cartridge comprises a plunger within the barrel. The plunger is configured for forcing the fluid drug solution through an outlet of the barrel. The outlet of the barrel may for instance be connected to an infusion set which is used to connect the fluid drug injection system to a person or living being. The barrel and plunger may be similar to the barrel and plunger of a syringe or ampoule.

The pump comprises an actuator for actuating the plunger to force the fluid drug solution through the outlet. The fluid drug injection system comprises a force sensor for force data during movement of the actuator. The force data may be recorded and/or analyzed as a function of time, position, and/or actuator velocity.

It has to be noted here that the force sensor may be located at any suitable position of the fluid drug injection system. For example, the force sensor may be integrated in the actuator. Another example is that the force sensor is located in between a housing of the fluid drug injection system and the barrel. The housing supports both, the barrel and the mechanism that is used to move the actuator. A further example is that the force sensor is located in between the housing and the mechanism that is used to move the actuator.

A force sensor located in between the barrel and the housing may have the advantage that it avoids electrically contacting a moveable component. The position of the force sensor in this embodiment is static and thus its operation may be less error prone than when the force sensor is integrated in the actuator and thus movable.

The method comprises the step of moving the actuator to contact or move the plunger. The method further comprises the steps of measuring the force data using the force sensor as the actuator is moved. The force data may be described and/or analyzed as a function of time and/or as a function of the actuator position or distance and/or as a function of actuator velocity. For instance, the force data may be correlated to the actual position of the actuator or it may be correlated to the velocity of the actuator as a function of time. The method further comprises the step of determining a feature signal from the force data. The feature signal is descriptive of a force modulation. The feature signal is, e.g., a characterization of any one of the following: a force modulation amplitude, a force modulation duration, and a force modulation number.

For example, the force data could be plotted as a function of time or position. There may be a modulation in the amplitude duration and a number of modulations which are visible in such a graph. These modulations represent an encoding of data which may be interpreted using the feature signal. The method further comprises the step of assigning the cartridge type to the fluid drug cartridge using the feature signal. For example, the fluid drug injection system could have a database or lookup table which is related to one or more of the various modulations of the feature signal. After the feature signal is measured and the modulation or modulation number is determined this may be used to directly lookup or find the cartridge type.

This may be beneficial because the feature signal can be used to identify the cartridge type. The cartridge type may for instance have different types of fluid drug solution or other mixtures which might be injected into the subject. The operation of the pump can be adjusted so that it operates appropriately for the particular type of fluid drug solution or cartridge. Fluid drug injection systems may already comprise a force sensor for measuring the force data. This may enable the determination of the cartridge type without needing additional hardware for a fluid drug injection system.

In another aspect, this disclosure provides for a fluid drug injection system comprising a pump configured for receiving a fluid drug cartridge. The fluid drug cartridge comprises a barrel filled with a fluid drug solution. The fluid drug cartridge comprises a plunger within the barrel. The plunger is configured for forcing the fluid drug solution through an outlet of the barrel. The pump comprises an actuator, e.g., a piston, for actuating the plunger to force the fluid drug solution through the outlet. The that is used to move the actuator comprises a force sensor for measuring force data. The force data is descriptive of the force applied to the plunger by the actuator.

The pump comprises a controller configured to control the actuator to move the actuator to contact or move the plunger. The controller is further configured to measure the force data using the force sensor. The controller is further configured to determine a feature signal from the force data. The feature signal is descriptive of a force modulation. The feature signal is, e.g., a characterization of any one of the following: a force modulation amplitude, a force modulation duration, a force modulation number and combinations thereof. The controller is further configured to assign the cartridge type to the fluid drug cartridge using the feature signal. The advantages of this embodiment have been previously discussed.

In another embodiment, the moving of the actuator to move the plunger is performed during a priming operation. This may be beneficial because the cartridge type can be assigned before any fluid drug solution is potentially injected.

In another embodiment, the force data is measured as a function of time or as a function of position of the plunger. The plunger is moved either at a constant velocity by an actuator or may be moved by an actuator that moves it as a series of discrete steps. As the force modulation occurs, the amount of force necessary to move the actuator changes. In some examples, the force data as a function of time or a function of position may be, as a practical matter, equivalent.

In another embodiment, the actuator is moved at a constant velocity or in discrete steps. For example a linear stepper or stepper motor could be used to move the actuator in a continuous or in a step wise manner. This embodiment may be beneficial because it provides a means of measuring the force needed to move the actuator either as a function of time and/or position.

In another embodiment, the cartridge type is assigned to the fluid drug cartridge by comparing the feature signal to example feature signals. For example, a pattern recognition algorithm could be used to compare the feature signal with a library of example feature signals. Simpler algorithms could also be used, such as a least squares fitting algorithm which compares how similar the feature signal is with each of the example feature signals.

In another embodiment, the example feature signals are contained within a lookup table or a database.

In another embodiment, the force modulation is a change in the measured force data. The force modulation is change or changes in the force that is recorded in the force data.

In another embodiment, the feature signal is a pattern that is identifiable within the force modulation.

In another embodiment, the plunger is formed from an elastomeric material and/or a combination of a rigid and an elastomeric material. For example a rigid core may be surrounded by an elastomeric o-ring seal.

In another embodiment, the pump in an insulin pump.

In another embodiment, the fluid drug injection system comprises a cartridge.

In another embodiment, the fluid drug injection system comprises one or more extensions within the barrel. The extensions are configured for causing the feature signal when the plunger or the actuator contacts the one or more extensions. This embodiment may be beneficial because the mechanical structure of the fluid drug cartridge may be used to positively identify it. Because the mechanical structure of the fluid drug cartridge has been modified it may prevent a situation where cartridges are misidentified.

In another embodiment, the plunger is shaped to form a cavity between the barrel and a side region of the plunger. The plunger comprises a plunger feeler. The plunger feeler is configured for contacting the one or more extensions to generate the feature signal when the actuator is moved. This embodiment may be beneficial because it may provide for a convenient mechanical means of providing the feature signal.

In another embodiment, the one or more extensions are within the cavity when the fluid drug cartridge is in a filled configuration. In an alternative, the one or more extensions are outside of the cavity before the fluid drug injection system has gone through a priming procedure. This may be beneficial because it may enable the one or more extensions to be used in calibrating or aligning the priming.

In another embodiment, the actuator itself contacts the one or more extensions. This may be beneficial because it may provide a means of providing for the feature signal without the plunger being in contact with extensions. This may improve the sealing properties of the plunger.

In another embodiment, the force modulation is determined by a number of the one or more extensions. This may be beneficial because a certain number of modulations may be easily identified within the feature signal.

In another embodiment, the force modulation is determined by a distance of the one or more extensions from the inner surface of the barrel. This may be beneficial because it provides a means of modulating the amount of force that the force sensor will measure. This may therefore modulate the amplitude of the feature signal.

In another embodiment, the force modulation is determined by a length of the one or more extensions in a plunger motion direction. This may be beneficial because the length of the one or more extensions may determine the length or period of a modulation in the feature signal.

In another embodiment, various combinations of the number of the one or more extensions, the distance of the one or more extensions and the length of the one or more extensions are combined in different ways. This may provide for redundant data within the feature signal which can be used to double check and ensure that the proper cartridge type is identified.

In another embodiment, the barrel comprises an inner surface. The one or more extensions may be a structuring of the inner surface. The structuring of the inner surface may be advantageous because it may provide for a means of providing for a complex or feature signals which are able to convey larger amounts of data.

In another embodiment, the one or more extensions are in contact with the fluid drug solution when the fluid drug cartridge is in a filled configuration. This may be advantageous because as the plunger moves into a particular position the texturing of the inner surface may begin to modulate the feature signal and provide information which is useful for the priming of the pump.

In another embodiment, the texturing of the inner surface is outside of the fluid drug solution when the fluid drug cartridge is in a filled configuration. This may be useful when the actuator is being moved to contact the plunger.

In another embodiment, the texturing is configured for determining the force modulation.

In another embodiment, the fluid drug system is configured for measuring the feature signal during a priming operation when the actuator moves the plunger. This embodiment may be beneficial because it may provide a means of identifying the fluid drug cartridge during the priming operation. As the priming operation is performed before the fluid drug is dispensed to a subject, the identification of the fluid drug cartridge is made before for example any basal dose of the fluid drug is provided.

In another embodiment, the barrel comprises an inlet for receiving the actuator. The actuator comprises an actuator feeler. The actuator feeler may for example be an extension that extends away from the surface of the actuator in a radial direction.

The inlet comprises a sleeve fitted within the barrel and attached to the inlet. The sleeve may for example be a tube or tube shaped structure which fits snugly or has a press fit for installing into the inner surface of the barrel.

The sleeve comprises one or more extensions that extend away from the inner surface of the barrel. The extensions are configured for causing the feature signal when the actuator feeler contacts the one or more extensions. This embodiment may be beneficial because a sleeve could be easily retrofitted or installed into a previously filled fluid drug cartridge or syringe. It could enable the modification of normal syringes for identification using the feature signal.

In another embodiment, the plunger comprises an actuator receptacle. The actuator comprises a plug surface. The actuator receptacle and the plug surface are configured for mating.

This embodiment may be beneficial because it may provide for a stable mechanical contact between the plunger and the actuator.

In another embodiment, the plug surface comprises an actuator feeler. The actuator receptacle comprises one or more extensions. The extensions are configured to cause the feature signal when the actuator feeler contacts the one or more extensions. For example, the one or more extensions in the actuator receptacle may be ribs or structures which are textured. As the actuator feeler and the plug surface are moved into the actuator receptacle, the feature signal can be determined. This may be beneficial because the cartridge type may be identified before the actuator receptacle and the plug surface have mated. This may provide for identification of the fluid drug cartridge before any fluid drug solution has been dispensed.

In another embodiment, the force modulation is determined by a distance of the one or more extensions from the surface of the actuator receptacle. This may be beneficial because it may determine the force modulation amplitude.

In another embodiment, the force modulation is determined at least partially by a number of the one or more extensions. This may determine the number of force modulations which are present in the feature signal.

In another embodiment, the force modulation is determined by a length of the one or more extensions in a plunger motion direction. This may be beneficial because it determines the force modulation duration.

In another embodiment, any of the above mentioned means of determining the force modulation may be combined.

In another embodiment, the fluid drug injection system is configured for measuring the feature signal during a force sniffing operation to place the actuator in contact with the plunger. A "force sniffing operation" as used herein encompasses the determination of when the actuator receptacle and the plug surface have mated by detecting an increase in the force measured by the force sensor and/or by the impact response measured by the force sensor.

In one example, the force response for different materials used in the construction of the cartridge is detected. As a concrete example, two cartridge types are differentiated by material used for constructing the plunger. In the first cartridge type the plunger is made from rubber. The second type of cartridge has a plunger made from a ceramic. As the two different plungers are impacted by the piston an impact response is measured. The rubber piston is constructed from an elastomer and therefore has a different impact response than the rigid ceramic piston. This enables the differentiation of these two different cartridge types.

In another example, when the measured force goes above a predetermined threshold in some cases it may be determined that the actuator receptacle and the plug surface have mated. Performing this during the force sniffing operation may be beneficial because it may provide for assigning of the cartridge type before the plunger has been moved and forced some of the fluid drug solution through the outlet.

In another embodiment, the feature signal has measured force ranges between 0.1 N and 5 N.

In another embodiment, the feature signal is measured within a range of 0.2 N and 4 N.

In another embodiment, the feature signal is measured between 0.3 N and 3 N.

In another aspect, this disclosure provides for a cartridge. The fluid drug cartridge comprises a barrel filled with an fluid drug solution. The fluid drug cartridge comprises a plunger within the barrel. The plunger is configured for forcing the fluid drug solution through an outlet of the barrel. The fluid drug cartridge is configured such that a force modulation is caused in an actuator configured for moving the plunger. This may take different forms. In some cases the force modulation is caused by motion between the plunger and the barrel. In other examples the force modulation is caused by interaction between the actuator itself and either the plunger or the barrel. The force modulation is, e.g., any one of the following: a force modulation amplitude, a force modulation duration, a force modulation number, and combinations thereof. The advantages of this cartridge have been previously discussed.

In another embodiment, the fluid drug cartridge comprises one or more extensions within the barrel. The extensions are configured for causing the first modulation when the plunger contacts the one or more extensions. The advantages of various modifications of this embodiment have been previously discussed. For example, the force modulation may be due to a texturing of the barrel. In other examples, the plunger may form a cavity with extensions that are then contacted by a feeler of the plunger.

In another embodiment, the plunger comprises an actuator receptacle. The actuator receptacle comprises one or more extensions. The extensions are configured for causing the force modulation when an actuator feeler of the actuator contacts the one or more extensions.

In another embodiment, the barrel comprises an inlet. The inlet comprises a sleeve fitted within the barrel and attached to or in contact with the inlet. The sleeve comprises one or more extensions. The extensions are configured for causing the force modulation when an actuator feeler of the actuator contacts the one or more extensions.

This example may for instance be similar to when the plunger comprises an actuator receptacle. The actuator receptacle may comprise a plug surface. The actuator receptacle and the plug surface may be configured for mating. The plug surface may comprise an actuator feeler. The actuator receptacle may comprise one or more extensions. The extensions are configured for causing the feature signal when the actuator feeler contacts the one or more extensions. The advantages of this embodiment have been previously discussed.

It is understood that one or more of the aforementioned embodiments may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Like numbered elements in these figures are either equivalent elements or perform the same function. Elements which have been discussed previously will not necessarily be discussed in later figures if the function is equivalent.

Figure 1:
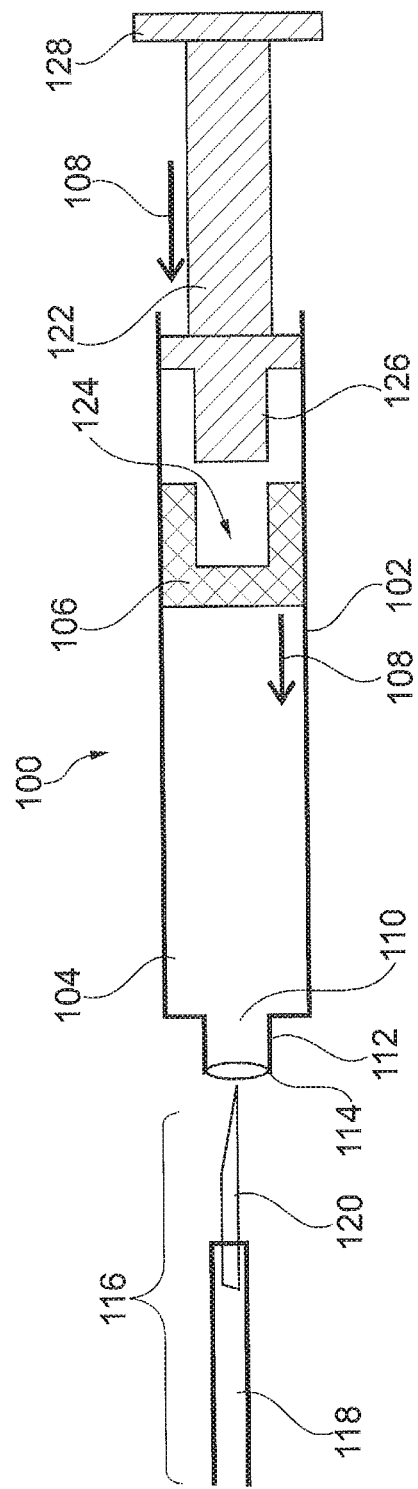
FIG. 1 illustrates an example of a fluid drug cartridge.

FIG. 1 shows an example of a cartridge 100 for use in a fluid drug injection system. The fluid drug cartridge 100 comprises a barrel 102 that is filled with a fluid drug solution 104. There is a plunger 106 that is configured for travelling in a plunger motion direction 108. When the plunger 106 is moved in the plunger motion direction 108 the fluid drug solution 104 may be forced out of an outlet 110. In this example, the barrel 102 narrows around the outlet 110 to form a head 112 to which an infusion set can be attached. In this example there is also an optional septum 114. The septum is an elastomeric material that may be pierced by a needle 120. An infusion set 116 may be attached to the head 112. In this example there is a tube 118 with a needle 120. The needle 120 is used to pierce the septum 114 and provide for a conduit for the fluid drug solution 104 to pass into the infusion set 116.

FIG. 1 also shows part of an actuator 122. The actuator is configured for moving also in the plunger motion direction 108 for the purpose of moving or actuating the plunger 106. In this example the plunger 106 comprises an actuator receptacle 124 for receiving a plug surface 126. The plug surface 126 is a surface on the actuator 122 that mates with the actuator receptacle 124. The actuator may comprise or be a piston.

In the following it is assumed without restriction to generality that the actuator 122 further comprises a force sensor 128 which may be used for sniffing or feeling (detecting) the amount of force applied to the plug surface 126 as a function of time or position. However, the force sensor 128 may also be located in between a housing of the fluid drug injection system and the barrel 102.

For example, the force sensor 128 may be used for sniffing to determine when the actuator receptacle 124 and the plug surface 126 have mated. Once they are in a mated position the amount of force necessary to move the actuator 122 may increase above a predetermined threshold.

Figure 2:
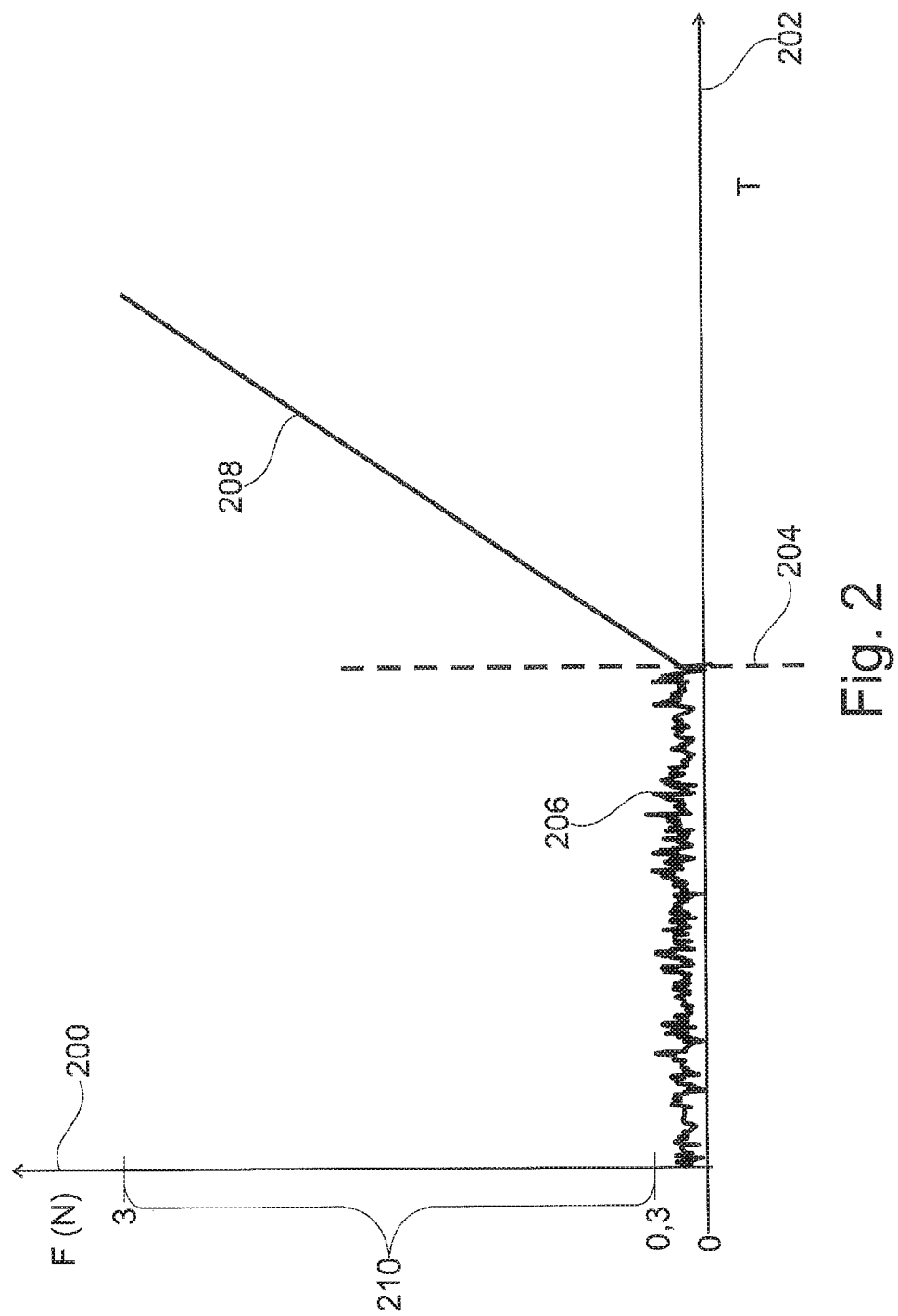
FIG. 2 illustrates an example of the time dependent force measured by a force sensor.

FIG. 2 shows a plot of the measured force 200 by the force sensor 120 of FIG. 1 as a function of time 202. The dashed line 204 indicates a time when the actuator receptacle begins to contact the plug surface. Before this time 204 the force sensor 128 measures a noise signal 206. To detect the time of the mating 204 a force sniffing signal 208 is measured. For example, a threshold force value can be set to determine when the actuator receptacle 124 and the plug surface 126 are considered to be mated. The force sensor 128 may have a particular dynamic range 210. In this example the dynamic range is between 0.3 N and 3 N. The 0.3 N represents the average or expected maximal amplitude of the noise signal 206. The threshold for when the actuator receptacle 124 and the plug surface 126 are considered to be mated would be set some place below 3 N which is the maximum force level which may be measured. Between the predetermined threshold and the noise ceiling which is 0.3 N there is a range where a feature signal can be measured which can be used to encode data. For example either texturing or putting bumps on the wall of the barrel 108 or within the actuator receptacle 124 may allow for a time varying force value which may be used for encoding data.

Figure 3:
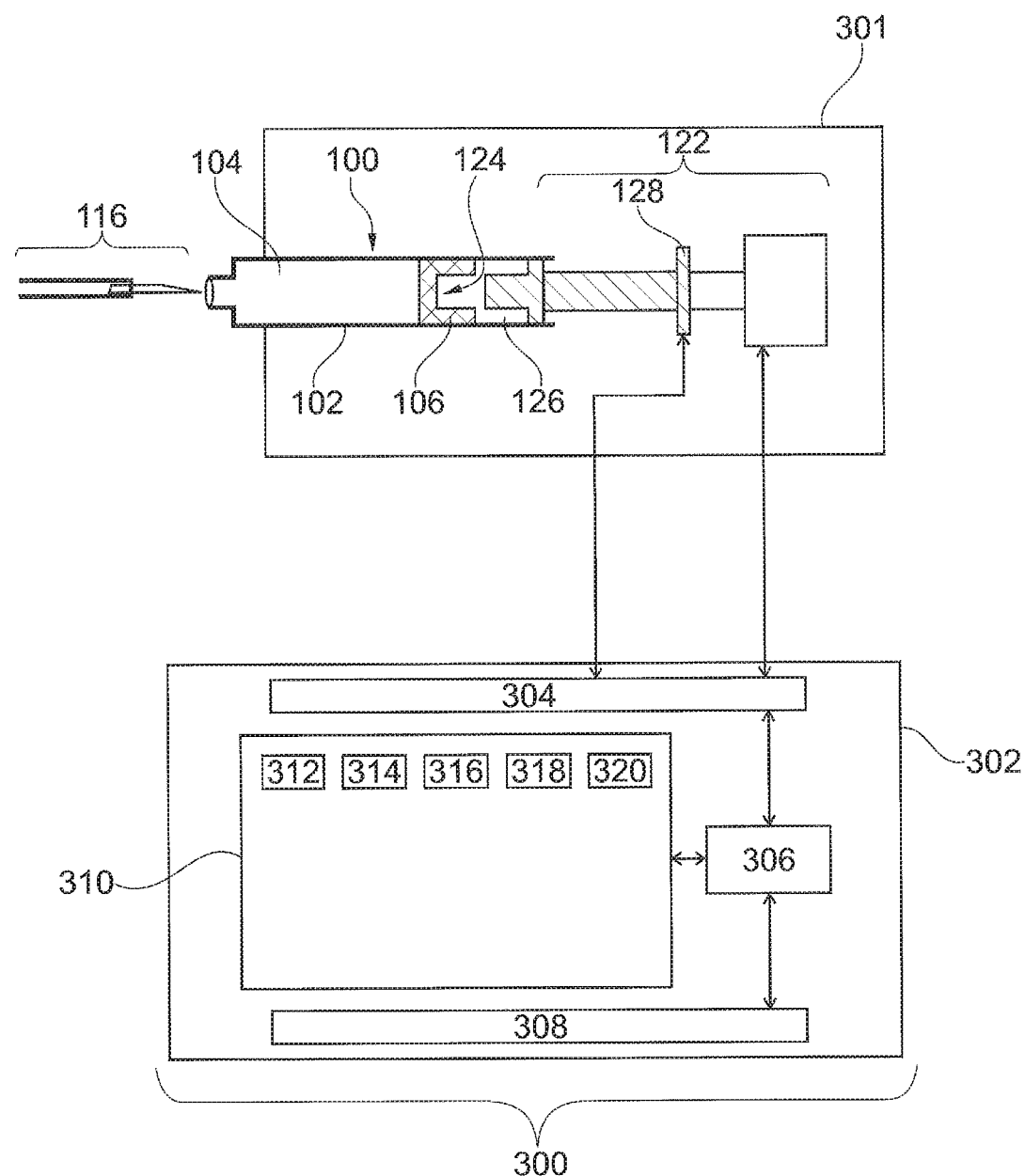
FIG. 3 illustrates an example of a fluid drug injection system.

FIG. 3 shows an example of a fluid drug injection system 300. The fluid drug injection system 300 comprises the actuator 122 and a controller 302. A cartridge 100 is seen as being installed into the fluid drug injection system 300. The controller 302 is configured for controlling the operation and function of the fluid drug injection system 300. The actuator 122 is part of a pump 301. The controller comprises a hardware interface 304 which enables it to control the various components of the fluid drug injection system 300. The controller 302 is further shown as containing a processor 306 which is in communication with the hardware interface 304, an optional user interface 308, and a memory 310. The user interface 308 may for instance be used for controlling the operation and function of the fluid drug injection system 300.

The memory 310 is shown as containing executable instructions 312. The executable instructions 312 enable the processor 306 to generate and receive commands for controlling the operation of the fluid drug injection system 300 and also to receive data from various components. The executable instructions 312 may contain instructions for such things as operating the pump 301 to administer a dose of the fluid drug solution 104 to a subject. The memory 310 is further shown as containing force data 314 that was measured using the force sensor 128. This may have been done when the actuator 122 was controlled to move the plug surface 126 to mate with the actuator receptacle 124 or afterwards during a priming operation. The memory 310 is further shown as containing a feature signal 316 that was extracted from the force data 314. The memory 310 is further shown as containing a database 318 which may contain a variety of feature signals or properties of feature signals which are indexed against a list or database of cartridge types. The memory 310 is further shown as containing a parameter describing a cartridge type 320. The cartridge type 320 was assigned to the fluid drug cartridge 100 based on the feature signal 316. The executable instructions 312 may for instance use the cartridge type 320 to determine the rate at which the fluid drug solution 104 is administered to a subject.

Even though the force sensor 128 is shown as being part of the actuator 122, it is also possible that the force sensor 128 is located in between the housing of the pump 301 and the actuator 122 or the barrel 102. Thus, the force sensor 128 is adapted to measure the reaction force of the actuator 122 on the housing.

Figure 4:
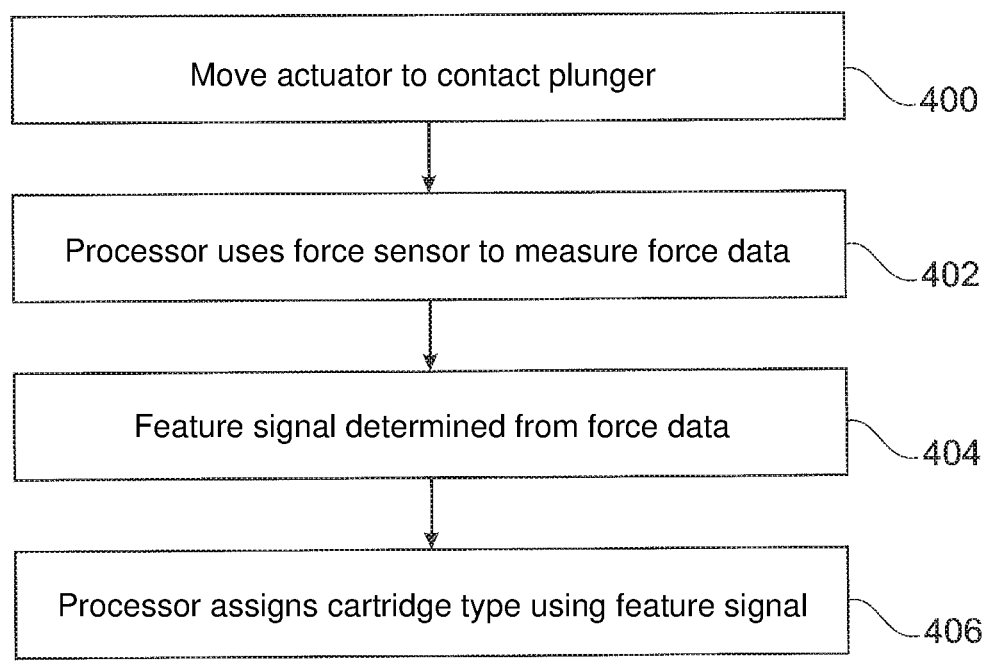
FIG. 4 shows a flow chart of a method of operating the fluid drug injection system of FIG. 3.

FIG. 4 shows a flowchart which illustrates a method of operating the fluid drug injection system 300 of FIG. 3. First in step 400 the actuator 122 is moved to contact the plunger 106 or it is moved to physically move the plunger 106. Next in step 402 the processor 306 uses the force sensor 128 to measure the force data 314. Next in step 404 the feature signal 316 is determined from the force data 314. The feature signal is descriptive of a force modulation. The feature signal is a characterization of any one of the following: a force modulation amplitude, a force modulation duration, a force modulation number, and combinations thereof. Next in step 406 the processor 306 assigns the cartridge type 320 using the feature signal 316. For instance the feature signal 316 or classification of the feature signal 316 can be used to extract the cartridge type 320 from the database 318.

Figure 5:
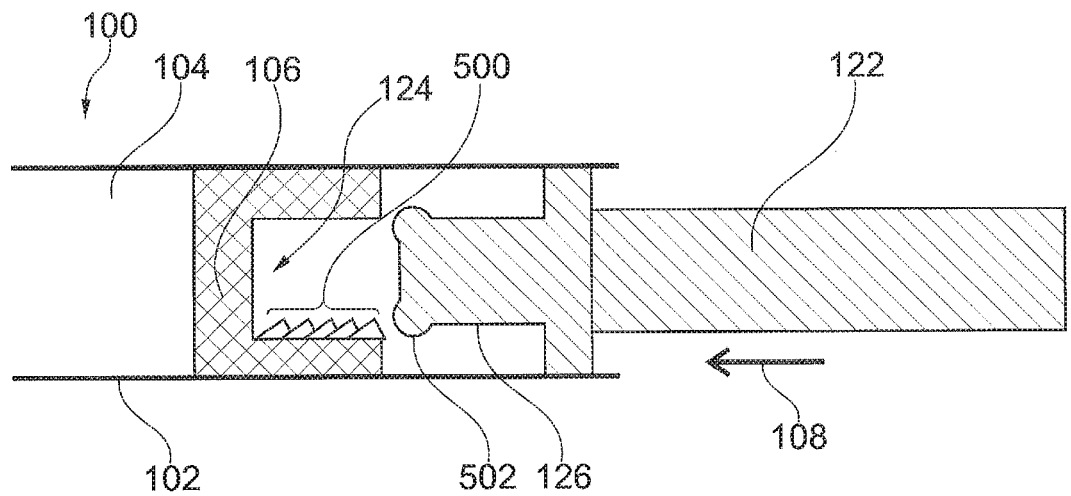
FIG. 5 illustrates a further example of a fluid drug cartridge.

FIG. 5 shows an example where the fluid drug cartridge 100 comprises a plunger 106 that has an actuator receptacle 124. The actuator 122 comprises a plug surface 126. The actuator receptacle 124 is configured for mating with the plug surface 126. In this example, it can be seen that the actuator receptacle comprises multiple extensions 500. In this example, there are five extensions which extend away from the surface of the actuator receptacle 124. The plug surface 126 comprises an actuator feeler 502. The actuator feeler 502 is configured to contact the extensions 500 when the plug surface 126 is being inserted into the actuator receptacle 124. As the actuator feeler 502 is forced over the extensions 500 it causes an increase and decrease in the amount of force necessary to move the plug surface 126 to mate with the actuator receptacle 124. For instance, during a force sniffing operation where the force is used to detect when the plug surface 126 has mated with the actuator receptacle 124 variations in the force caused by the extensions 500 can be used to encode an identifier for the fluid drug cartridge 100.

Figure 6:
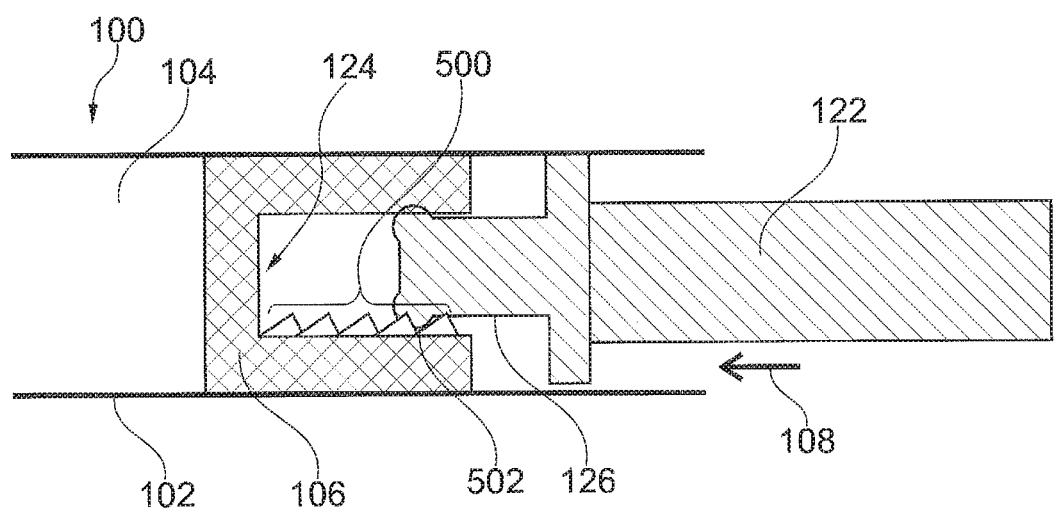
FIG. 6 further illustrates the example fluid drug cartridge in FIG. 5.

FIG. 6 shows the same cartridge and actuator 122 that is similar to the cartridge and actuator shown in FIG. 5. In this example the plug surface 126 has been partially inserted into the actuator receptacle 124. Additionally, the multiple extensions 500 are spaced further apart that what is shown in FIG. 5. As a function of distance, the extensions are spaced in FIG. 6 further apart than shown in FIG. 5. The amplitude frequency of the force modulation will therefore be lower for the cartridge of FIG. 6.

Figure 7:
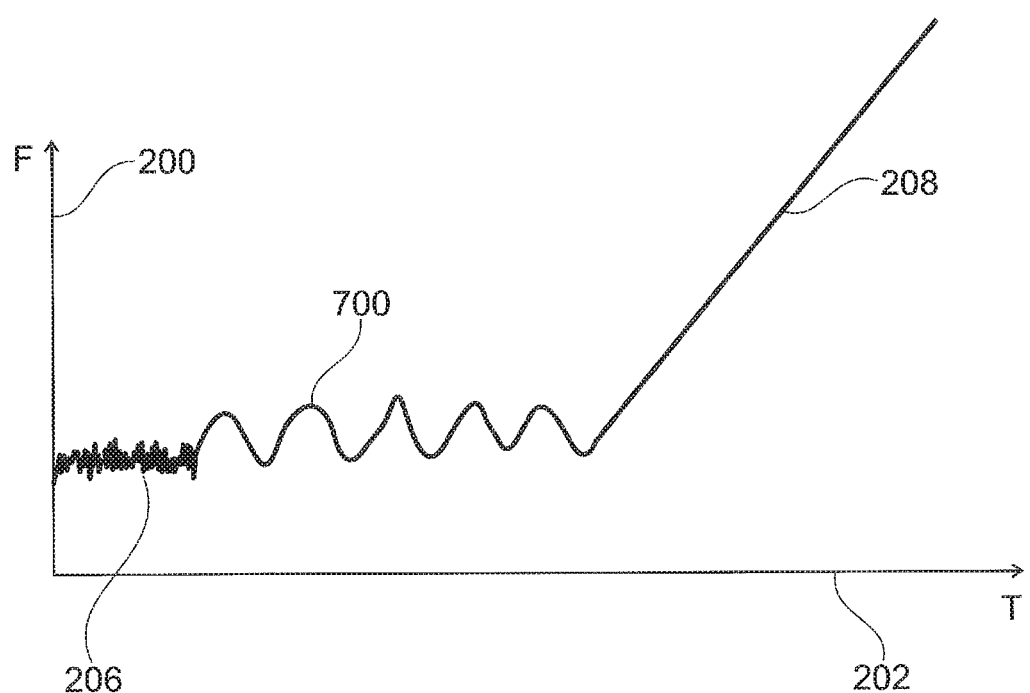
FIG. 7 illustrates a force vs. time plot for the fluid drug cartridge of FIGS. 5 and 6.

FIG. 7 shows a plot of force 200 versus time 202 measured by the force sensor as the plug surface 126 in FIG. 5 is inserted into the actuator receptacle 124. Before the actuator feeler 502 contacts the extensions 500 a noise region 206 is measured. Then as the actuator feeler 502 is drawn across the various extensions 500 this results in a feature signal 700. After the plug surface 126 is mated into the actuator receptacle 124 the force 208 begins to increase steadily. It can be seen that the feature signal has five ripples or bumps. These correspond to the five ripples or bumps depicted in FIGS. 5 and 6 as the extensions 500.

Figure 8:
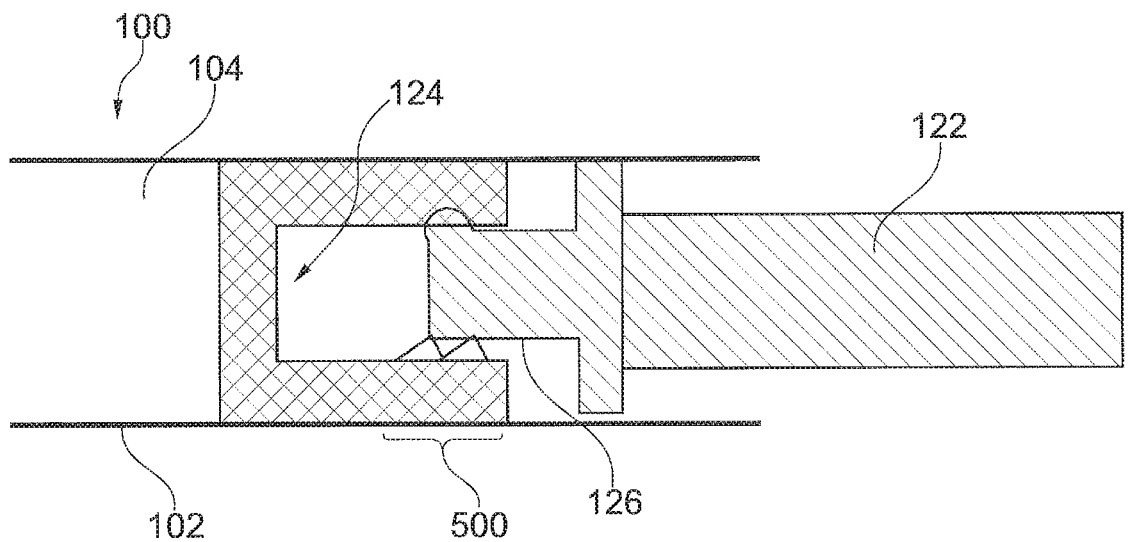
FIG. 8 illustrates a further example of a fluid drug cartridge.

FIG. 8 shows an example that is similar to the example depicted in FIGS. 5 and 6. However, in FIG. 8 the number of the extensions 500 has been reduced. In this example there are only two extensions.

Figure 9:
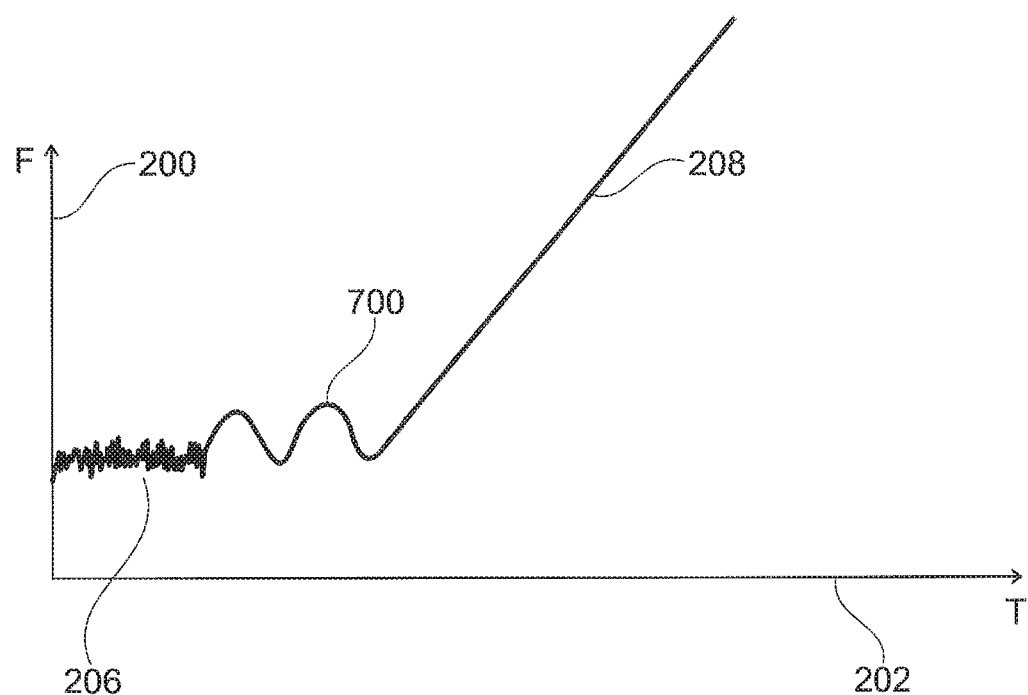
FIG. 9 illustrates a force vs. time plot for the fluid drug cartridge of FIG. 8.

FIG. 9 shows the force 200 versus time plot 202 for the fluid drug cartridge 100 depicted in FIG. 8. It is similar to the chart shown in FIG. 7 except that in this case there are only two bumps in the feature signal 700. The number of bumps in the feature signal 700 may be considered to be the force modulation number. It can be seen by comparing FIGS. 7 and 9 that controlling the number of extensions 500 can be used to encode data which can be extracted from the feature signal 700. The number of the force modulations may therefore be used to encode a cartridge type.

Figure 10:
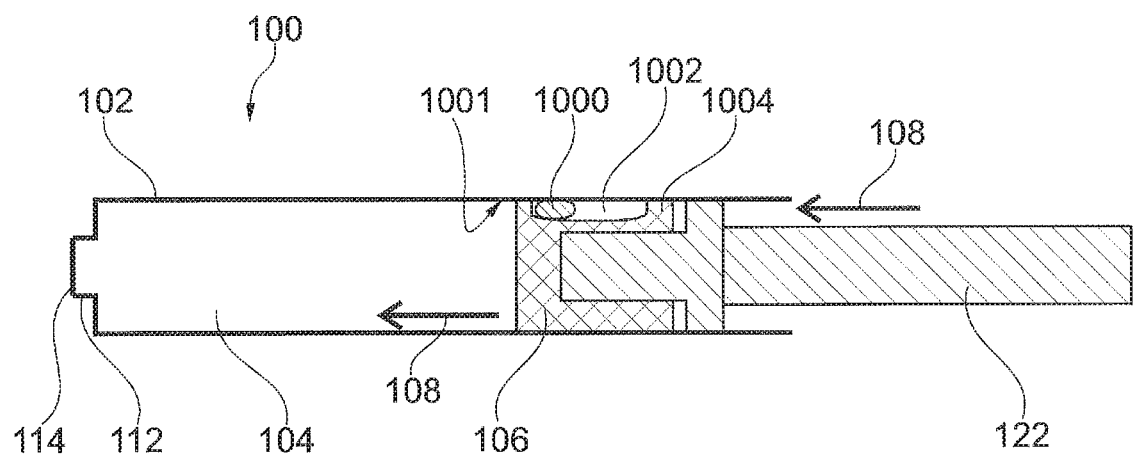
FIG. 10 illustrates a further example of a fluid drug cartridge.

FIG. 10 shows a further example of the fluid drug cartridge 100. In this example there is an extension 100 that is attached to an inside surface 1001 of the barrel 108. The plunger 106 has a cavity 102 which is positioned for accommodating the extension 1000 when the fluid drug cartridge 100 is in a filled configuration. In this example, the fluid drug cartridge 100 is fully filled. As the actuator 122 moves in the plunger motion direction 108 the extension 1000 is able to freely move within the cavity 1002 until it contacts an extension of the plunger 106. This extension is the plunger feeler 104. The plunger feeler 1004 contacts the extension 1000 and the amount of force necessary to continue moving the plunger increases.

Figure 11:
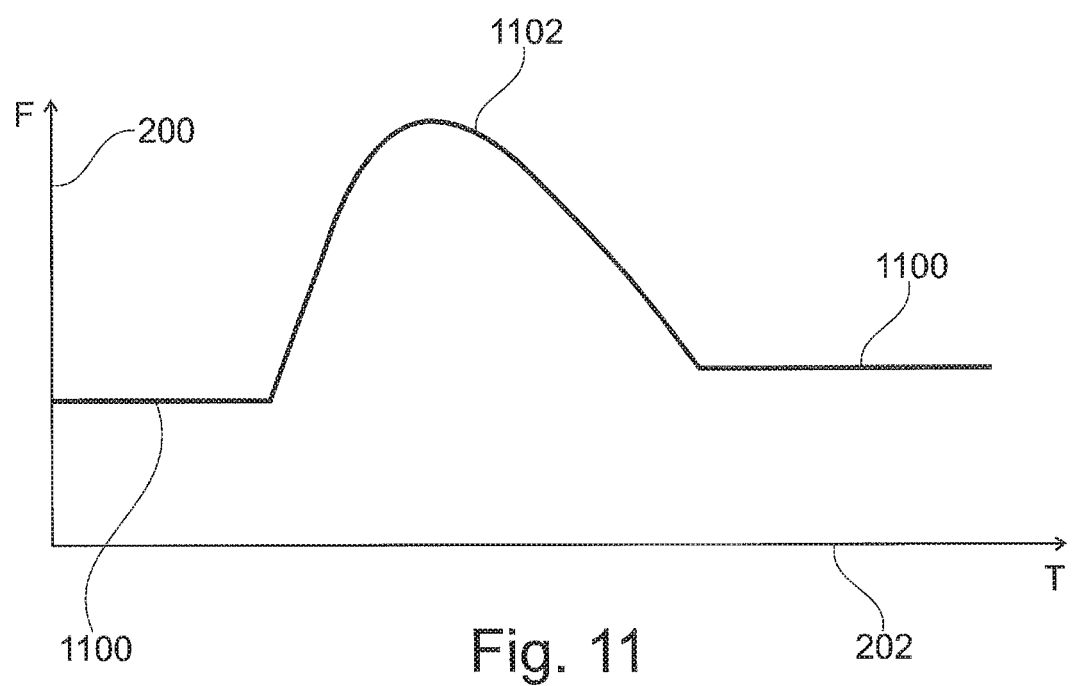
FIG. 11 illustrates a force vs. time plot for the fluid drug cartridge of FIG. 10.

FIG. 11 shows a force versus time plot for the fluid drug cartridge 100. In this example the actuator 122 has already mated with the plunger 106. The regions marked 1000 indicate where the force is due to frictional forces and also the force of forcing the fluid drug solution 104 from the fluid drug cartridge 100. The region marked 1102 is the feature signal. This indicates the time period when the plunger feeler 1004 contacts the extension 1000 and needs to be pushed over the extension 1000. After the plunger feeler 1004 has been cleared of the extension 1000 the force returns back to the frictional force level 1100.

As with the previous example the number of bumps or extensions 1000 may be controlled. Additionally the length to control the duration of the feature signal 1102 may be controlled and also how high the extension 1000 extends from the inside surface 1001 of the barrel 108.

Figure 12:
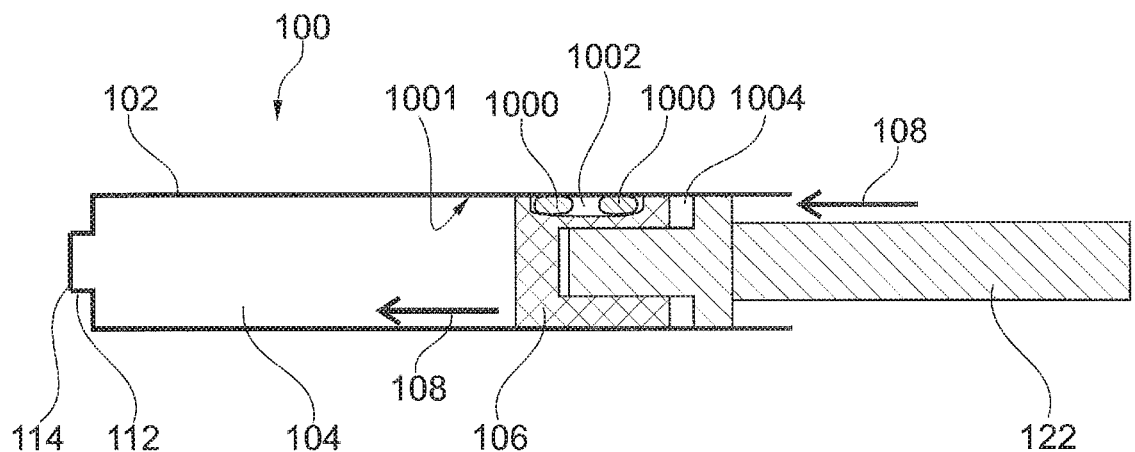
FIG. 12 illustrates a further example of a fluid drug cartridge.

FIG. 12 shows a further example of a cartridge. The example shown in FIG. 12 is similar to that shown in FIG. 10. However in this example there are two extensions 1000. This results in a feature signal which has two modulations.

Figure 13:
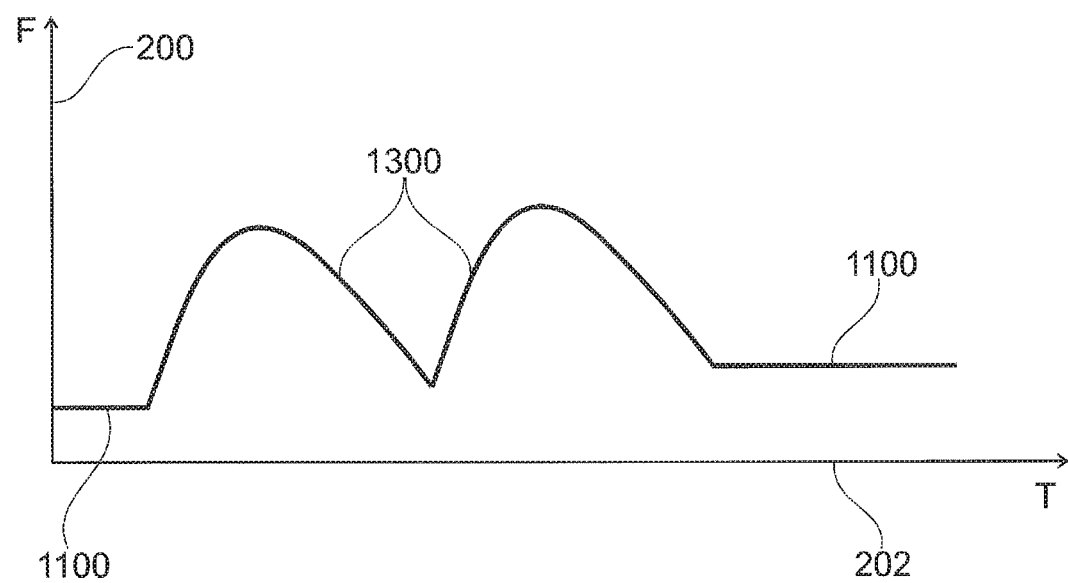
FIG. 13 illustrates a force vs. time plot for the fluid drug cartridge of FIG. 12.

FIG. 13 shows the force 200 versus time plot for the fluid drug cartridge 100 of FIG. 12. It can be seen that the feature signal 1300 contains two modulations. These two modulations 1300 correspond to the two extensions 100 shown in FIG. 12. It is clear from FIGS. 11 and 13 that the number of extensions 1100 can be used to encode data.

Figure 14:
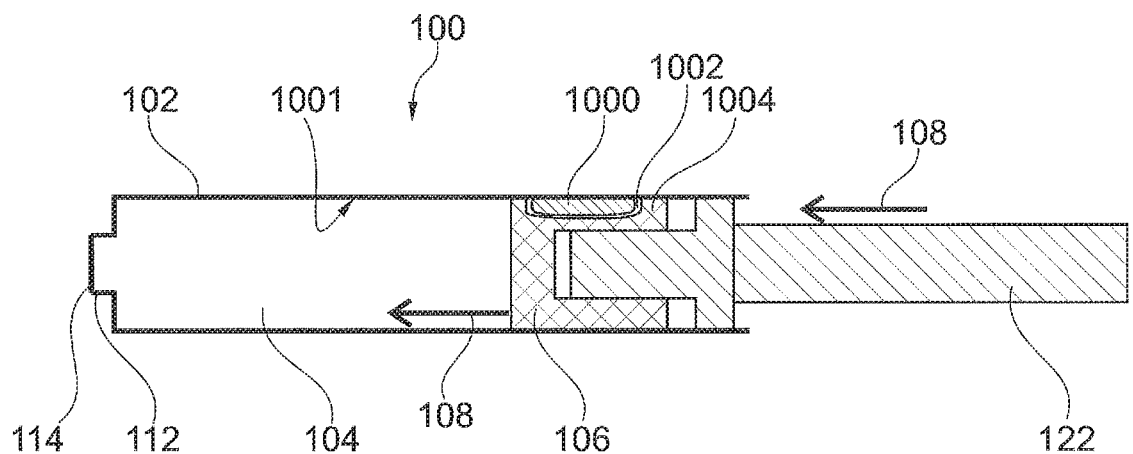
FIG. 14 illustrates a further example of a fluid drug cartridge.

FIG. 14 illustrates a further example of the fluid drug cartridge 100. In this example the fluid drug cartridge 100 is similar to that depicted in FIG. 10. However in this example the extension 1000 is wider or longer in the plunger motion direction than it is in FIG. 10. This causes a noticeable difference in the feature signal.

Figure 15:
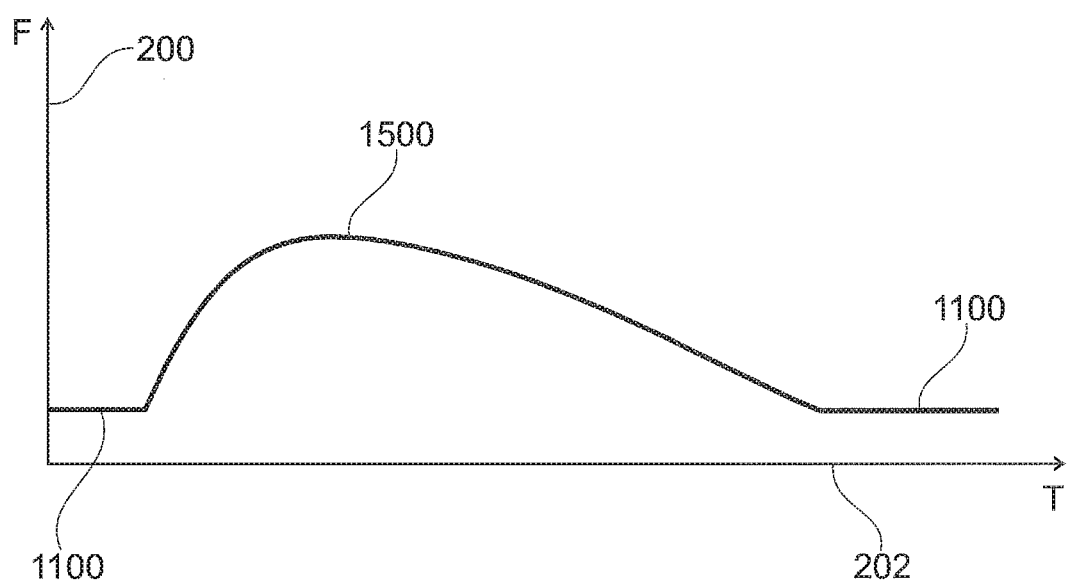
FIG. 15 illustrates a force vs. time plot for the fluid drug cartridge of FIG. 14.

The force 200 versus time plot 202 for the fluid drug cartridge of FIG. 14 is illustrated in FIG. 15. Because the extension 1000 is longer in the plunger motion direction 108 the feature signal 1500 is wider than the feature signal 1102 depicted in FIG. 11. This width or duration of the feature signal 1500 can also be used to encode data or to differentiate different cartridges 100.

Figure 16:
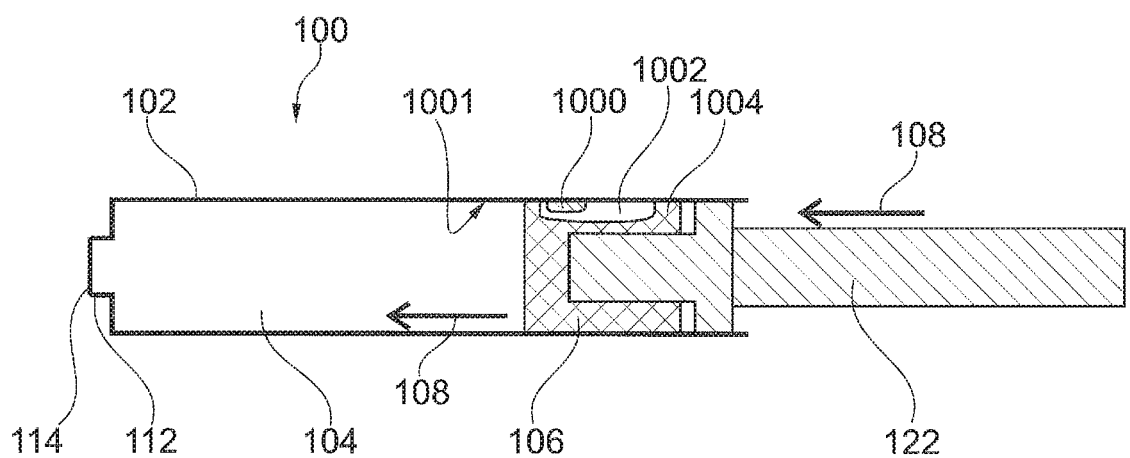
FIG. 16 illustrates a further example of a fluid drug cartridge.

FIG. 16 shows a further example of a cartridge 100. The fluid drug cartridge 100 in FIG. 16 is similar to the fluid drug cartridge 100 in FIG. 10. However in the example shown in FIG. 16 the extension 100 is shorter or shallower than the extension in FIG. 10. The extension 1000 in FIG. 16 does not extend as far from the inner surface 1001 of the barrel 102 as does the extension 1000 in FIG. 10. This results in a measurable difference in the amplitude of the feature signal. This effect is illustrated by comparing FIG. 17 (below) with FIG. 11.

Figure 17:
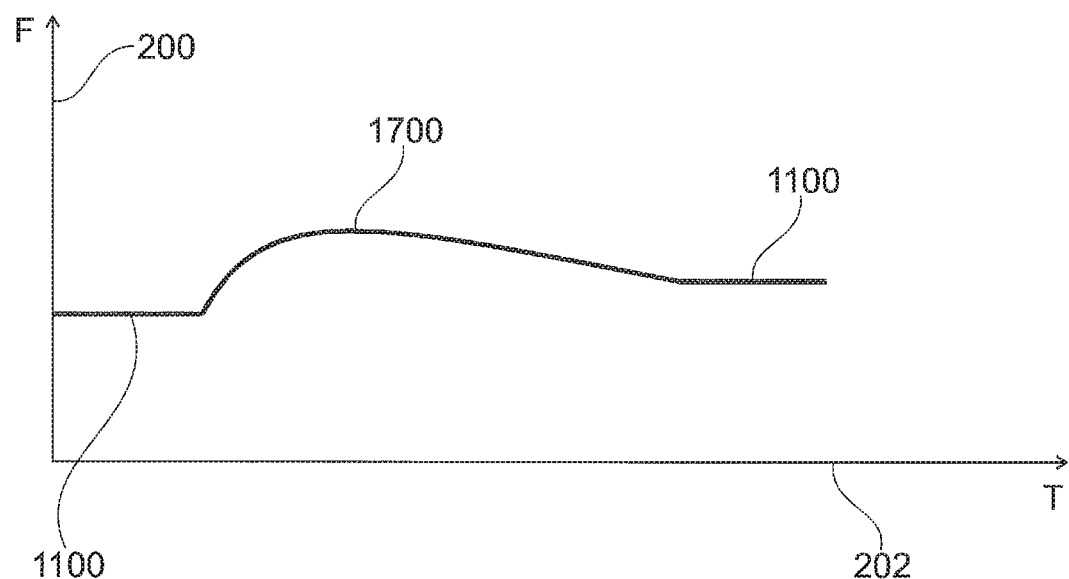
FIG. 17 illustrates a force vs. time plot for the fluid drug cartridge of FIG. 16.

FIG. 17 shows the force 200 versus time plot 202 for the fluid drug cartridge 100 shown in FIG. 16. In FIG. 17 the feature signal 1700 still only shows one modulation because there is only one extension 1000. However, when one compares FIGS. 17 and 11 it can be seen that the amplitude of the modulation in FIG. 17 has decreased in comparison to the modulation amplitude shown in FIG. 11. FIG. 17 illustrates that the distance that the extension 1000 extends from the inner surface 1001 of the barrel 102 can be used to control the amplitude of the feature signal 1700. This may also be used to encode data and/or to identify different cartridge types.

Figure 18:
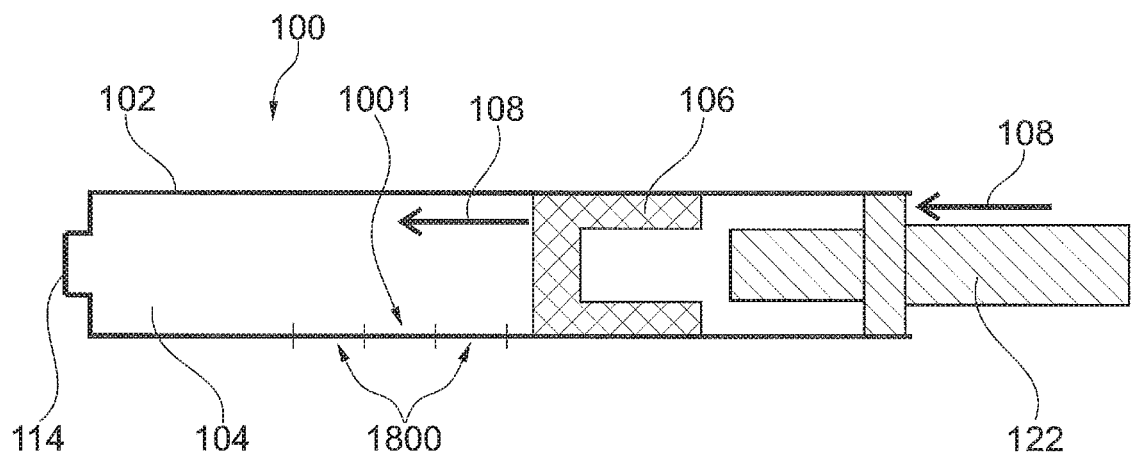
FIG. 18 illustrates a further example of a fluid drug cartridge.

FIG. 18 shows a further example of a cartridge 100. In this example there are several textured regions 1800 on the inside surface 1001 of the barrel 102. As the plunger 106 contacts the textured regions 1800 this causes a feature signal because the textured regions increase or decrease the amount of friction between the plunger 106 and the barrel 102. The textured regions 1800 could for example comprise small extensions or grooves in the inside surface 1001 of the barrel 102.

Figure 19:
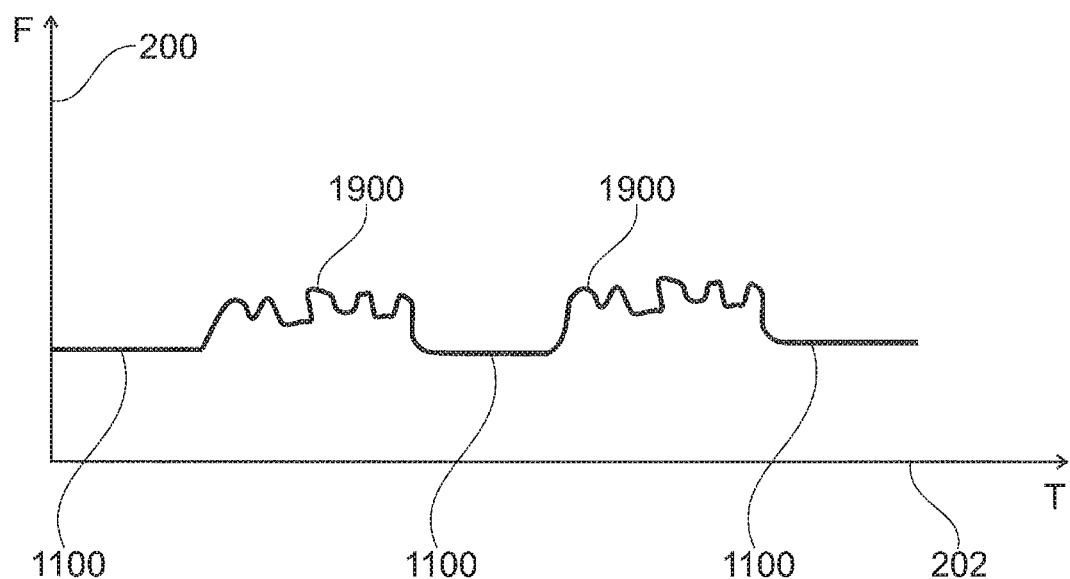
FIG. 19 illustrates a force vs. time plot for the fluid drug cartridge of FIG. 18.

FIG. 19 shows an example force 200 versus time 202 plot for the fluid drug cartridge 100 of FIG. 18. In FIG. 18 there are two textured regions 1800. This then corresponds to the two feature signals 1900 illustrated in FIG. 19. Data could be encoded in the shape of the feature signals 1900, the amplitude of the feature signals, and also the number of feature signals.

Figure 20:
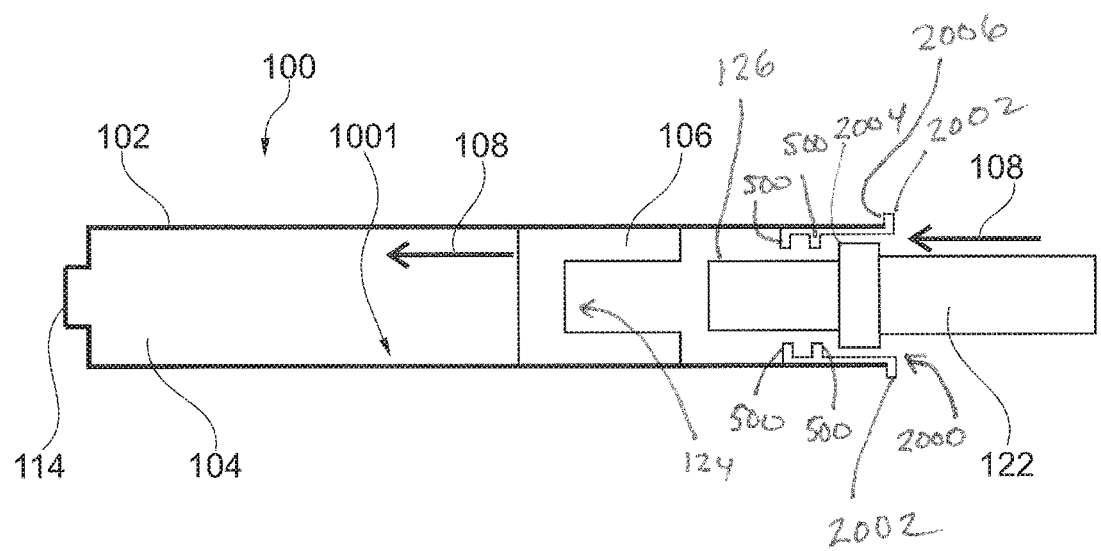
FIG. 20 illustrates a further example of a fluid drug cartridge.

FIG. 20 shows a further example of a cartridge 100. The barrel 102 has an inlet 2000. A sleeve 2002 has been inserted into the barrel 102 and is in contact with the inlet 2000 of the barrel 102. The sleeve 2002 is a tube that fits flush with the inner surface 1001. The sleeve 2002 is further seen as comprising a stop 2006 that contacts the inlet 2000 and controls how far the sleeve 2002 can be inserted into the barrel 102.

The actuator 122 comprises an actuator feeler 2004. The actuator feeler 2004 is an extension of the actuator 122 that extends towards the inner surface 1001. The sleeve two extensions 500. As the actuator moves the one or more extensions 500 will contact the actuator feeler. This causes the force needed to move the actuator 122 to increase. This increase in the force is a force modulation. The extensions are therefore configured for causing the feature signal when the actuator feeler contacts the one or more extensions.

In the example shown in FIG. 20, there are two extensions. In other examples there could be more or fewer extensions. The distance and width of the extensions may also be used to modify the feature signal.

Figure 21:
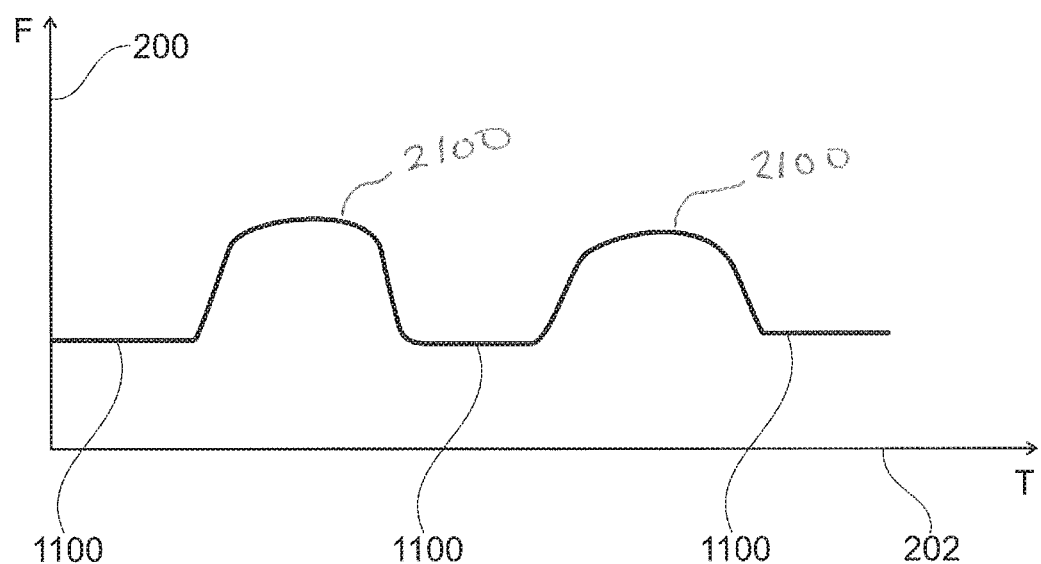
FIG. 21 illustrates a force vs. time plot for the fluid drug cartridge of FIG. 22.

FIG. 21 shows an example force 200 versus time 202 plot for the fluid drug cartridge 100 of FIG. 20. In FIG. 20 there are two extensions 500. This then corresponds to the two increases in force 2100. These two increases in force 2100 can be considered to be two feature signals. Data could be encoded in the shape of the feature signals 2100, the amplitude, the number, and the spacing of the increases in the force 2100 can be modified by changing the number and/or shape of the extensions 500 that are in the inside of the sleeve 2002.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS 100 cartridge
102 barrel
104 fluid drug solution
106 plunger
108 plunger motion direction
110 outlet
112 head
114 septum
116 part of infusion set
118 tube
120 needle
122 actuator
124 actuator receptacle
126 plug surface
128 force sensor
200 measured force
202 time
204 time of mating
206 noise signal
208 force sniffing signal
300 fluid drug injection system
301 pump
302 controller
304 hardware interface
306 processor
308 user interface
310 memory
312 executable instructions
314 force data
316 feature signal
318 database
320 parameter describing cartridge type
404 move the actuator to contact the plunger or move the plunger
402 measure the force data using the force sensor
404 determine a feature signal from the force data
406 assign the cartridge type to the fluid drug cartridge using the feature signal
500 extensions
502 actuator feeler
700 feature signal
1000 extension
1001 inside surface
1002 cavity
1004 plunger feeler
1100 frictional force
1102 feature signal
1300 feature signal
1700 feature signal
1800 textured regions
1900 feature signal
2000 inlet
2002 sleeve
2004 actuator feeler
2006 stop
2100 feature signal

What is claimed is:

1. A method of determining a cartridge type in a fluid drug injection system, the drug injection system having a pump that receives different fluid drug cartridges that each have a barrel filled with a fluid drug solution and a plunger within the barrel configured for forcing the fluid drug solution through an outlet of the barrel, the method comprising:
    moving an actuator of the pump to contact or to move the plunger of the fluid drug cartridge;
    using a force sensor to measure force data during movement of the actuator, wherein the force data is descriptive of the force applied to the plunger by the actuator;
    determining a feature signal from the force data, the feature signal being descriptive of a force modulation; and
    assigning the cartridge type to the fluid drug cartridge using the feature signal.

2. The method of claim 1, wherein the moving of the actuator to move the plunger is performed during a priming operation.

3. The method of claim 1, wherein the force data is measured as a function of time or as a function of position of the plunger.

4. The method of claim 1, wherein the actuator is moved at a constant velocity or in discrete steps.

5. The method of claim 1, wherein the cartridge type is assigned to the fluid drug cartridge by comparing the feature signal to example feature signals.

6. The method of claim 5, wherein the example feature signals are contained within a lookup table or a database.

7. The method of claim 1, wherein the force modulation is a change in the measured force data.

8. The method of claim 7, wherein the feature signal is a pattern that is identifiable within the force modulation.

9. A fluid drug injection system, comprising:
    a pump configured to receive a fluid drug cartridge that has a barrel filled with a fluid drug solution and that further includes a plunger within the barrel, wherein the plunger is configured for forcing the fluid drug solution through an outlet of the barrel;

an actuator configured for actuating the plunger;

a force sensor configured for measuring force data that is descriptive of the force applied to the plunger by the actuator; and a controller configured to:
(i) move the actuator to contact or move the plunger;
(ii) measure force data using the force sensor during movement of the actuator;
(iii) determine a feature signal from the force data, wherein the feature signal is descriptive of a force modulation; and
(iv) assign a cartridge type to the fluid drug cartridge using the feature signal.

10. The fluid drug injection system of claim 9, wherein the fluid drug injection system includes the fluid drug cartridge.

11. The fluid drug injection system of claim 10, wherein the fluid drug injection system comprises one or more extensions within the barrel that are configured for causing the feature signal when the plunger or the actuator contacts the one or more extensions.

12. The fluid drug injection system of claim 11, wherein the plunger forms a cavity between the barrel and a side region of the plunger, wherein the plunger comprises a plunger feeler configured for contacting the one or more extensions to generate the feature signal when the actuator is moved.

13. The fluid drug injection system of claim 12, wherein the force modulation is determined by any one or combinations of the following: a number of the one or more extensions, a distance of the one or more extensions from an inner surface of the barrel, a length of the one or more extensions in a plunger motion direction.

14. The fluid drug injection system of claim 11, wherein the barrel comprises an inner surface and the one or more extensions is a texturing of the inner surface, wherein the one or more extensions are in contact with the fluid drug solution when the fluid drug cartridge is in a filled configuration.

15. The fluid drug injection system of claim 14, wherein the texturing is configured for generating the force modulation.

16. The fluid drug injection system of claim 9, wherein:
the barrel comprises an inlet for receiving the actuator and the actuator comprises an actuator feeler;
a sleeve is fitted within the barrel and is attached to the inlet; and
the sleeve comprises one or more extensions configured for causing the feature signal when the actuator feeler contacts the one or more extensions.

17. The fluid drug injection system of claim 9, wherein:
the plunger comprises an actuator receptacle;
the actuator comprises a plug surface;
the actuator receptacle and the plug surface are configured for mating;
the plug surface comprises an actuator feeler;
the actuator receptacle comprises one or more extensions; and
the extensions are configured for causing the feature signal when the actuator feeler contacts the one or more extensions.

18. The fluid drug injection system of claim 16, wherein the force modulation is determined by any one or combinations of the following: a number of the one or more extensions determines the force modulation number, a distance of the one or more extensions from a surface of the actuator receptacle determines the force modulation amplitude, a length of the one or more extensions in a plunger motion direction determines the force modulation duration.

19. The fluid drug injection system of claim 16, wherein the fluid drug injection system is configured for measuring the feature signal during a force sniffing operation to position the actuator in contact with the plunger.

20. The fluid drug injection system of claim 9, wherein the feature signal is a characterization of any one of the following: a force modulation amplitude, a force modulation duration, a force modulation number.

21. The fluid drug injection system of claim 9, wherein the controller is configured to move the actuator to move the plunger during a priming operation.

22. The fluid drug injection system of claim 9, wherein the controller is configured to measure the force data as a function of time or as a function of position of the plunger.

23. The fluid drug injection system of claim 9, wherein the actuator is configured to move at a constant velocity or in discrete steps.

24. The fluid drug injection system of claim 9, wherein the controller is configured to assign the cartridge type to the fluid drug cartridge by comparing the feature signal to example feature signals.

25. The fluid drug injection system of claim 24, wherein the example feature signals are contained within a lookup table or a database.

26. The fluid drug injection system of claim 9, wherein the force modulation is a change in the measured force data.

27. The fluid drug injection system of claim 26, wherein the feature signal is a pattern that is identifiable within the force modulation.

* * * * *